United States Patent
Tajima et al.

(10) Patent No.: US 7,089,779 B2
(45) Date of Patent: Aug. 15, 2006

(54) PORTABLE GAS DETECTOR

(75) Inventors: Shuji Tajima, Tokyo (JP); Yasunori Takei, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 0 days.

(21) Appl. No.: 10/914,889

(22) Filed: Aug. 9, 2004

(65) Prior Publication Data

US 2005/0092063 A1 May 5, 2005

(30) Foreign Application Priority Data

Oct. 31, 2003 (JP) .............................. 2003-373013

(51) Int. Cl.
*G01N 7/00* (2006.01)
(52) U.S. Cl. ..................................... 73/23.2
(58) Field of Classification Search ............... 73/23.31, 73/23.2, 29.05; 417/63; 422/68.1
See application file for complete search history.

(56) References Cited

U.S. PATENT DOCUMENTS

| | | | | |
|---|---|---|---|---|
| 6,606,897 B1 * | 8/2003 | Koyano et al. | ............... | 73/23.2 |
| 6,712,586 B1 * | 3/2004 | Koyano et al. | ............... | 417/63 |
| 2003/0138329 A1 * | 7/2003 | Koyano et al. | ............... | 417/63 |
| 2004/0062684 A1 * | 4/2004 | McGee et al. | ............. | 422/68.1 |

FOREIGN PATENT DOCUMENTS

JP       2002-116169 A       4/2002

* cited by examiner

*Primary Examiner*—Hezron Williams
*Assistant Examiner*—Tamiko Bellamy
(74) *Attorney, Agent, or Firm*—Frishauf, Holtz, Goodman & Chick, P.C.

(57) ABSTRACT

The invention provides a portable gas detector of a novel structure that is easy to be fabricated as a small-sized one handy to carry and high in convenience for use. The portable gas detector has a housing in the form of a slim and flat box holdable by grasping with a hand, and a foreside half portion in the interior of he housing is provided as a functional part region, and a rear half portion in the interior of the housing is provided as a battery part region. In the functional part region, one of 5 gas sensors is arranged at a curved portion in a gas sensor-arranging region of an L shape as a whole, and 2 gas sensors are arranged in a row in both lateral and vertical directions of the above gas sensor, respectively. A gas sucking means is arranged in a region, the 2 directions of which is sectioned by the gas sensor-arranging region.

10 Claims, 9 Drawing Sheets

PORTABLE GAS DETECTOR

BACKGROUND OF THE INVENTION

1. Field of the Invention

The present invention relates to a portable gas detector, and particularly to a portable gas detector equipped with a gas sucking means for introducing a gas to be detected into it and capable of detecting plural kinds of gas components.

2. Description of the Background Art

There are generally frequent occasions when it may be possible in, for example, underground job sites or gateways, or other places where persons enter, or working regions that air in an environmental atmosphere is in a dangerous state, or will become a dangerous state, such as occasions when hazardous gases such as carbon monoxide and hydrogen sulfide gases may possibly be contained in air in such an environment, or when the oxygen gas concentration in air may possibly be lowered.

When the air in the environmental atmosphere has become a dangerous state to persons due to high concentration of the dangerous gases contained or low oxygen gas concentration, it is necessary to immediately sense the fact.

From such a demand, there have heretofore been proposed various types of portable gas detectors. Some of these portable gas detectors are provided with a plurality off gas sensors respectively detecting gas components different from each other in such a manner that the plurality of the gas components can be detected at the said time (see, for example, Japanese Patent Application Laid-Open No. 2002-116169

In such a portable gas detector, however, a method, in which a gas to be detected that is, for example, air in an object space to conduct gas detection, is introduced into a gas sensor by natural diffusion, is utilized. It may be however necessary in some cases to introduce the gas to be detected into the gas sensors by forcedly sucking the gas to be detected by a gas sucking means such as a pump.

In a portable gas detector having a plurality of built-in gas sensors, however, it generally becomes large in size and heavy in weight when the gas sucking means is provided in the body of the gas detector and hence involves problems that it is considerably unhandy to carry and is a great obstacle to practice the intended work or the like.

SUMMARY OF THE INVENTION

The present invention has been made on the basis of the foregoing circumstances and has as its object the provision of a portable gas detector of a novel structure that is easy to be fabricated as a small-sized one handy to carry and high in convenience for use.

According to the present invention, there is thus provided a portable gas detector comprising a housing in the form of a slim and flat box holdable by grasping with a hand, and a foreside half portion in the interior of the housing is provided as a functional part region, in which functional members related to a gas detecting operation are arranged, and a rear half portion in the interior of the housing is provided as a battery part region, in which a power source for driving the functional members is arranged, wherein in the functional part region, 5 gas sensors are arranged in a state that one of them has been located at a curved portion in a gas sensor-arranging region of an L shape as a whole, and 2 gas sensors have been located in a row in both lateral and vertical directions of the above gas sensor, respectively, and a gas sucking means to feed a gas to be detected from the outside to the respective gas sensors by suction is arranged in a region, the 2 directions of which is sectioned by the gas sensor-arranging region.

In the portable gas detector according to the present invention, the detector may be so constructed that the respective gas sensors are held in a state fixed by a sensor holder, in which sensor holding parts for holding the gas sensors in a state arranged in a plane direction have been formed, and a sensor cap, in the interior of which a gas flowing path successively linked with the respective sensor holding parts has been formed.

In the portable gas detector according to the present invention, the detector may also be so constructed that at least one of the plurality of the gas sensors is composed of a contact combustion type gas sensor element, and voltage of 4.5 V is supplied from the power source for driving.

In the portable gas detector according to the present invention, the detector may further preferably be so constructed that a battery chamber is formed in the battery part region in the interior of the housing so as to be opened to the back surface of the housing, and either one of 3 rod-like dry cells or a chargeable battery pack formed by holding 3 chargeable batteries having the same external shape as the dry cell by a holding frame member in a state arranged in parallel is installed in the battery chamber exchangeably with the other.

Still further, in the portable gas detector according to the present invention, the detector may preferably be so constructed that a pressure sensor is arranged in the region, the 2 directions of which is sectioned by the gas sensor-arranging region, in a state connected to an exhaust-side flowing path of the gas sucking means.

According to the portable gas detector of the present invention, the housing fundamentally has the form holdable by grasping with a hand, and all the necessary component members are rationally arranged in a state that a dead space within the housing is reduced as much as possible, so that the gas detector itself can be fabricated into a small-sized one while surely retaining necessary functions. Accordingly, excellent portability and high convenience for use are achieved.

In addition, the detector has the so-called common battery chamber formed in such a manner that either one of dry cells or a chargeable battery pack can be installed exchangeably with the other, whereby both dry cells (primary cells) and chargeable batteries (secondary batteries) can be used without using any attachment such as an adaptor.

Since comparatively great power is ensured as a power source for driving, at least one of the gas sensors can be provided as one of the contact combustion type, so that the degree of freedom of selection of detectable gas components becomes high, and high convenience for use is achieved.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described with reference to the drawings.

Figure 1:
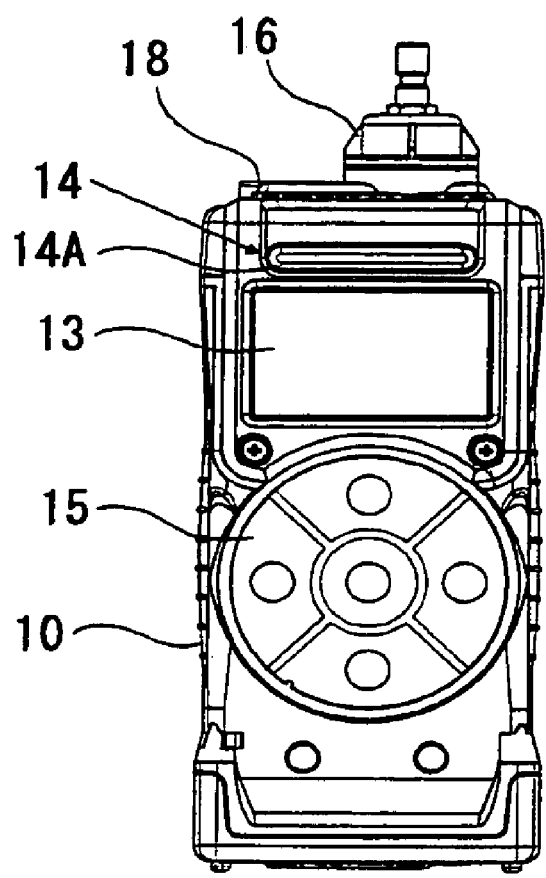
FIG. 1 is a front elevation illustrating the appearance of a constructional example of a portable gas detector according to the present invention.
Figure 2:
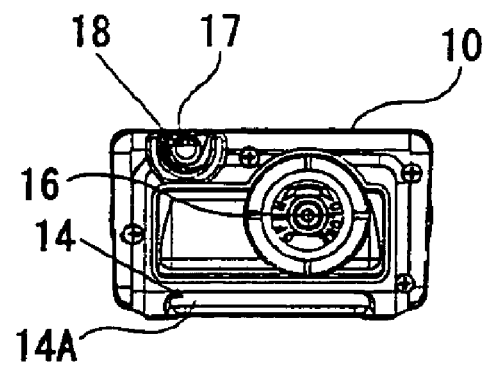
FIG. 2 is a foreside view of the portable gas detector shown in FIG. 1.
Figure 3:
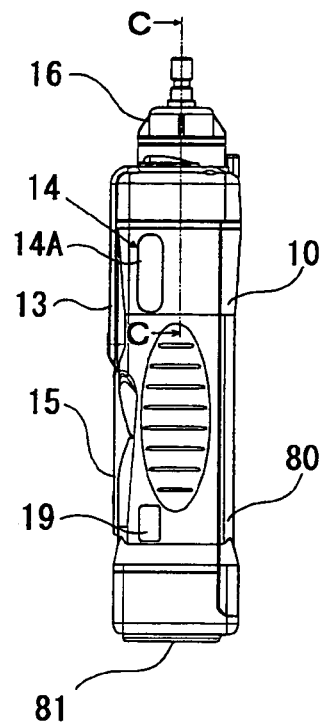
FIG. 3 is a side elevation of the portable gas detector shown in FIG. 1.
Figure 4:
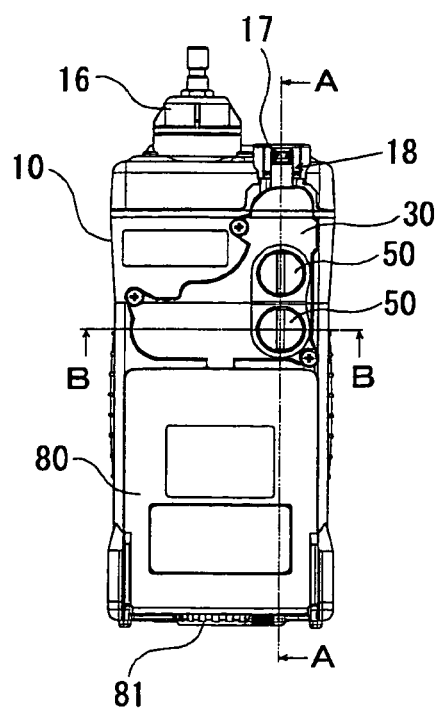
FIG. 4 is a back view of the portable gas detector shown in FIG. 1.
Figure 5:
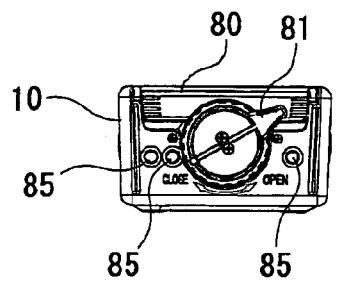
FIG. 5 is a rear elevation of the portable gas detector shown in FIG. 1.
Figure 6:
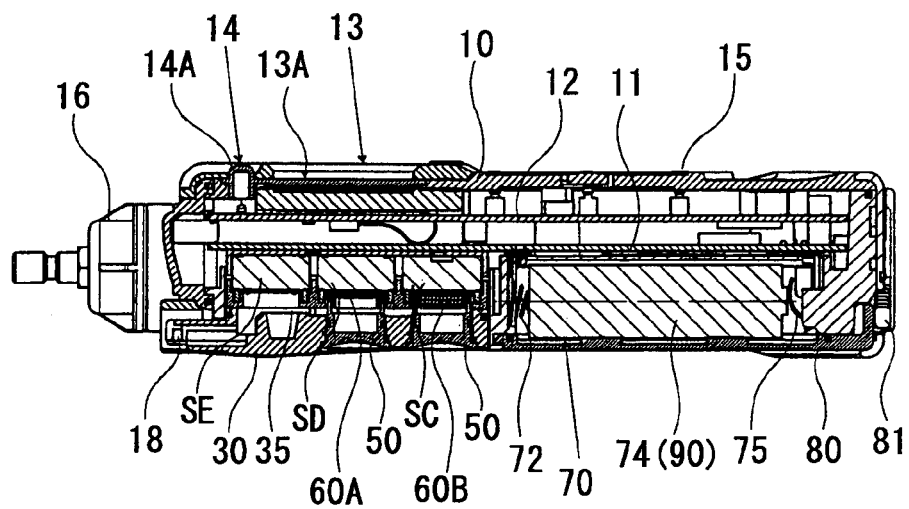
FIG. 6 is a cross-sectional view taken along line A—A in FIG. 4.
Figure 7:
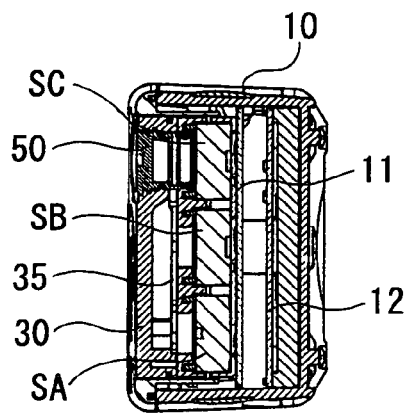
FIG. 7 is a cross-sectional view taken along line B—B in FIG. 4.
Figure 8:
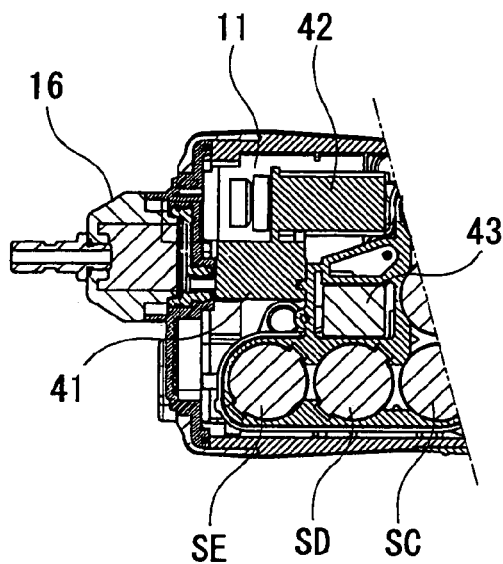
FIG. 8 is a cross-sectional view taken along line C—C in FIG. 3.

FIG. 1 is a front elevation illustrating the appearance of a constructional example of a portable gas detector according to the present invention, FIG. 2 is a foreside view of the portable gas detector shown in FIG. 1, FIG. 3 is a side elevation of the portable gas detector shown in FIG. 1, FIG. 4 is a back view elevation of the portable gas detector shown in FIG. 1, FIG. 5 is a rear elevation of the portable gas detector shown in FIG. 1, FIG. 6 is a cross-sectional view taken along line A—A in FIG. 4, FIG. 7 is a cross-sectional view taken along line B—B in FIG. 4, and FIG. 8 is a cross-sectional view taken along line C—C in FIG. 3.

This portable gas detector (hereinafter referred to as "gas detector" merely) is equipped with a housing 10 in the form of a slim and flat box holdable by grasping with a hand. On the front surface side in the interior of the housing 10, a circuit board 11 for control including a gas detection signal-processing circuit for processing signals from gas sensors and a circuit board 12 including a circuit for power supply and a circuit for charging are arranged in parallel with each other so as to extend along the flat surface of the housing 10.

A foreside or distal side half portion in the interior of the housing 10 is provided as a functional part region, in which functional members related to a gas detecting operation are arranged, and a rear half portion is provided as a battery part region. In FIGS. 1 to 8, reference numeral 16 indicates a filter unit for introducing air in an object space in a state that dust has been removed, and reference numeral 18 designates a gas discharging part equipped with a gas discharging port 17 opened to the back surface.

On the front surface side of the circuit board 11 for control in the functional part region, a panel-like display mechanism 13A composed of, for example, a liquid crystal display panel, on which the kinds and concentrations of gases detected are displayed, is arranged, whereby a display part 13 is formed in the front surface of the housing 10, and light emitting parts 14 for alarm are formed respectively in a fore-end or distal and surface, a front surface region continued from the fore-end surface and both side surface regions of the housing 10. The light emitting parts 14 for alarm are each formed by a light source composed of a light emitting diode (not illustrated) and an aperture plate 14A held by the housing 10 so as to cover the light source. The light emitting parts 14 for alarm are formed respectively in the fore-end surface, the front surface region continued form the fore-end surface and both side surface regions of the housing 10, whereby, in reality, an alarm operation by light emission of the light emitting parts 14 for alarm can be quickly observed irrespective of the posture of the gas detector, so that proper measures can be immediately taken, and high safety can be achieved.

An operating button 15 is provided at a lower half portion in the front surface of the housing 10.

On the back side of the circuit board 11 for control in the functional part region, are arranged a plurality of gas sensors and a pump unit that is a gas sucking means to successively feed a gas to be detected from the outside to the respective gas sensors by suction.

Figure 9:
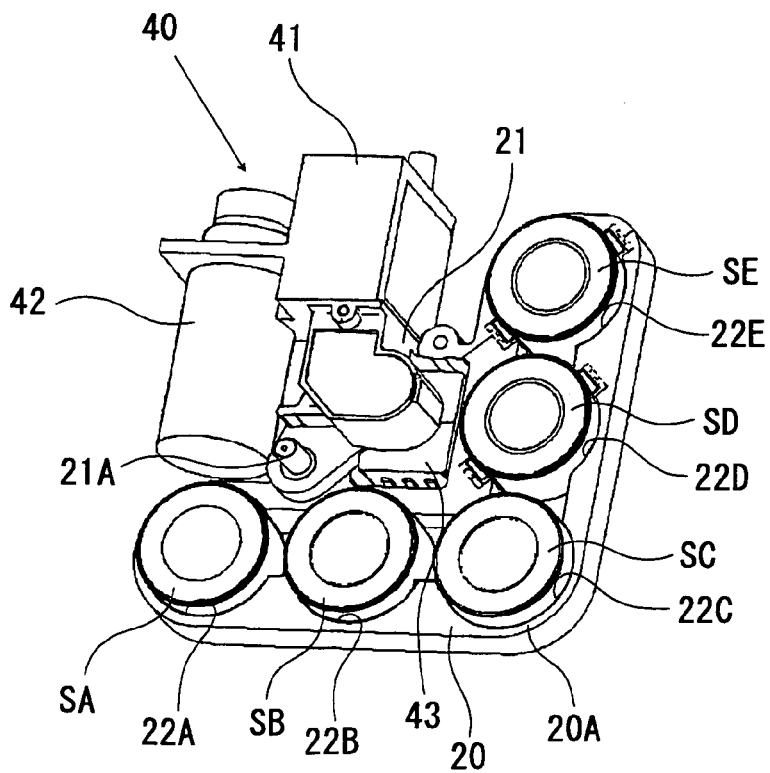
FIG. 9 is a perspective view illustrating the construction of a sensor holder in a state that gas sensors and a pump unit have been installed in the sensor holder.

Specifically described, as illustrated in FIG. 9, 5 button type gas sensors SA to SE are fixed and held by a sensor cap 30 installed from the back side in a state received to a sensor holder 20 having a gas sensor-arranging region of an L-shape as a whole, and the pump unit 40 is installed and arranged in a pump unit-installing part 21 formed at a corner approaching the gas sensor-arranging region in a region, the 2 directions of which is sectioned by the gas sensor-arranging region. Incidentally, the sensor cap 30 is omitted in FIG. 9 for convenience' sake.

The sensor holder 20 is formed of a substantially L-shaped plate as a whole, a gas sensor-receiving recess 22C is formed at a curved portion 20A thereof, and 2 gas sensor-receiving recesses 22A and 22B and 2 gas sensor-receiving recesses 22D and 22E are formed in a row in lateral and vertical directions of the gas sensor-receiving recess 22C, respectively, whereby the L-shaped gas sensor-arranging region is formed. This sensor holder 20 is fixed and arranged on the circuit board 11 for control.

The pump unit-installing part 21 functions as a gas flowing path-forming member, and a gas to be detected ejected from a gas suction pump 41 is ejected from a gas-ejecting pipe 21A provided so as to project and extend upward through a gas flowing path formed within the pump unit-installing part 21. In the present invention, for example, a pipe, the opening diameter of which is smaller than the inner diameter of the gas flowing path, is used as the gas-ejecting pipe 21A, whereby the gas to be detected is ejected in a pressurized state.

As the gas sensors, may be used gas sensor elements according to the kinds of object gases to be detected. In the gas detector described above, however, a contact combustion type gas sensor element is used as at least one of the 5 gas sensors.

As an example of a combination of the gas sensors, a gas sensor SA for detecting oxygen gas, which is composed of, for example, a galvanic cell type gas sensor element, a gas sensor SB for detecting hydrogen sulfide gas, which is composed of, for example, a controlled potential electrolysis type gas sensor element, a gas sensor SC for detecting carbon monoxide gas, which is composed of, for example, a controlled potential electrolysis type gas sensor element, a gas sensor SD for detecting hydrocarbon gases in a measurement range of % LEL concentration (level of explosion limit), which is composed of, for example, a contact combustion type gas sensor element, and a gas sensor SE for detecting hydrocarbon gases in a measurement range of volume %, which is composed of, for example, a thermal conductivity type gas sensor element, are used in order from the upstream side of a flowing direction of a gas to be detected.

The pump unit 40 is formed by, for example, a diaphragm type gas suction pump 41 and a pump-driving motor 42 provided integrally with the gas suction pump 41. The gas suction pump 41 is installed at a fore-end of the pump unit-installing part 21 in the sensor holder 20, and the pump-driving motor 42 is arranged along a side surface of the pump unit-installing part 21 in such a manner that a driving shaft thereof extends in foreside and rear directions, thereby the pump unit is held in a state substantially not projected from a peripheral edge (foreside and side edges) of the circuit board 11 for control. In the present invention, that having performance capable of feeding a gas to be detected at a flow rate of, for example, 0.2 to 0.5 liters/min is used as the gas suction pump 41.

In the gas detector, a pressure sensor 43 is provided in a state held by the pump unit-installing part 21 in the sensor holder 20 as illustrated in FIGS. 8 and 9. When the flow rate of a gas introduced is lowered due to, for example, suction of water, and lowering of the exhaust pressure of the gas to be detected by the gas suction pump 41 is detected by the pressure sensor 43, the operation of the gas suction pump 41 is forcedly stopped.

Figure 10:
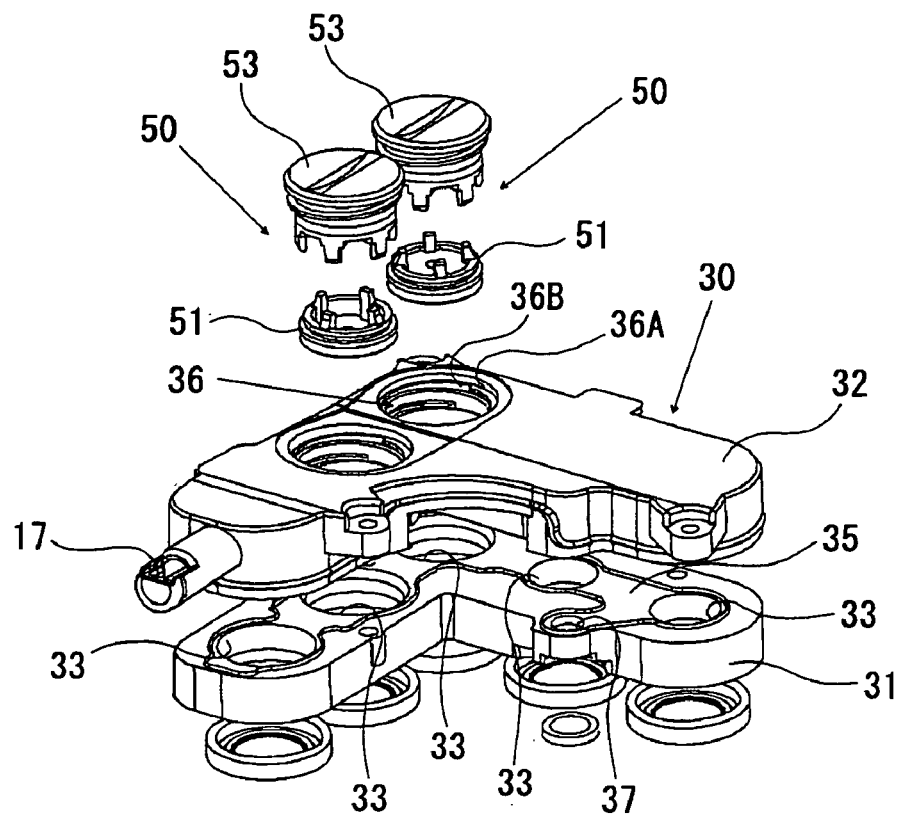
FIG. 10 is an exploded perspective view illustrating the construction of a sensor cap.

The sensor cap 30 is formed by integrally stacking an internal-side cap member 31 and an external-side cap member 32 as illustrated in FIG. 10.

In the internal-side cap member 31, gas inlet passages 33 extending through in a thickness-wise direction thereof are formed at positions corresponding to the respective gas sensors SA to SE. Parts of the internal-side cap member 31 and the external-side cap member 32, specifically, parts of surfaces of the internal-side cap member 31 and the external-side cap member 32, which come into contact with each other, are removed along the gas sensor-arranging region, whereby a gas flowing path 35 is formed. In FIG. 10, reference numeral 37 indicates a joint of the gas-ejecting pipe 21A in the sensor holder 20.

In the sensor cap 30, are formed filter-installing parts 36, in which a filter assembly 50 having a function of adsorbing any other interfering gas component than the object gas component to be detected by the gas sensor is installed.

In this embodiment, through-holes 36A extending through in the thickness-wise direction of the sensor cap 30 are formed at respective positions corresponding to the gas sensor SC for detecting carbon monoxide gas arranged at the curved portion 20A of the gas sensor-arranging region and the gas sensor SD for detecting hydrocarbon gases in a measurement range of % LEL, which is arranged adjacently to the gas sensor SC on the downstream side of the flowing direction of a gas to be detected, and a spiral groove 36B is formed in an inner peripheral surface of each of the through-holes 36A, thereby forming the filter-installing parts 36.

Figure 11:
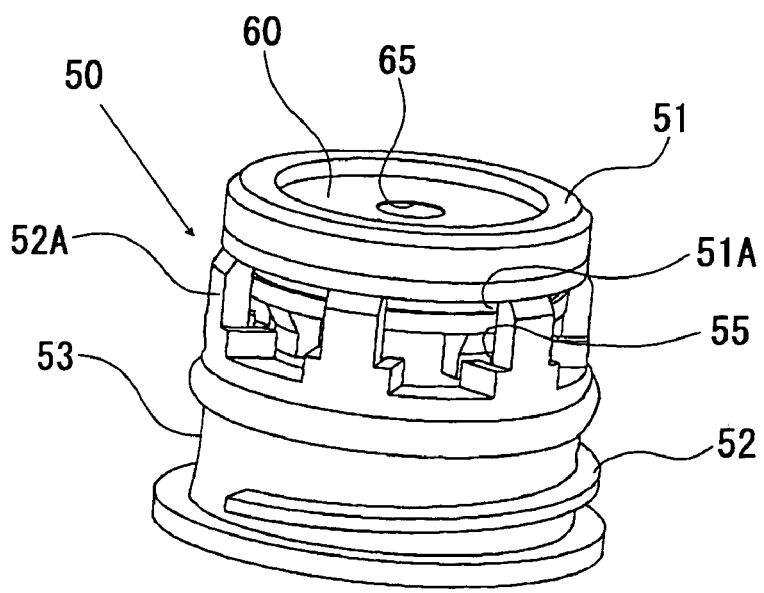
FIG. 11 is a perspective view illustrating the construction of a filter assembly.

As illustrated in FIG. 11, the filter assembly 50 is formed by a filter laminate 60, which adsorbs and removes an interfering gas component related to the gas sensors, a filter holder 51 holding the filter laminate 60, and a filter cap 53 composed of, for example, a transparent resin and having the form of a substantially cylinder with a bottom, on the peripheral wall of which a projected portion 52 fitting to the spiral groove 36B in the filter-installing part 36 is formed. Engaging claws 52A formed at an opening edge of the filter cap 53 so as to project and extend outward are engaged with a circular groove 51A formed at an end-side portion in the peripheral wall of the filter holder 51, whereby the filter holder 51 is detachably fitted to the filter cap 53.

In the state that the filter holder 51 has been fitted to the filter cap 53, the projected portion 52 of the filter cap 53 is screwed into the spiral groove 36B of the filter-installing part 36 in the sensor cap 30 in a state that the filter laminate 60 is located within the gas inlet passage 33 of the internal-side cap member 31, whereby the whole filter assembly 50 is detachably fitted into the sensor cap 30. Reference numeral 55 indicates openings for introducing a gas, and these openings are formed at plural positions in a state separated from each other in a peripheral direction.

The filter laminate 60 is formed by, for example, stacking functional membranes having at least a function of adsorbing the interfering gas component related to the gas sensors in a state intervened between 2 outer membranes.

Figure 12:
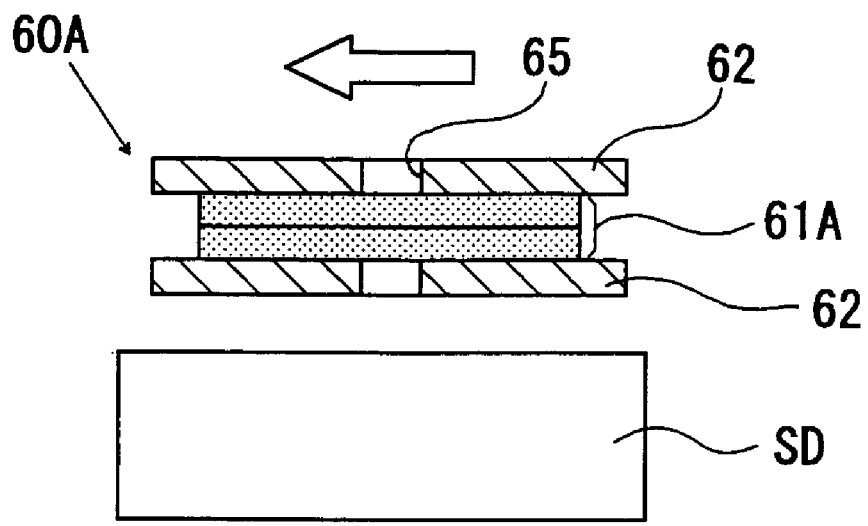
FIG. 12 is a cross-sectional view illustrating the construction of an exemplary filter laminate related to a gas sensor for detecting hydrocarbon gases in a measurement range of % LEL.

For example, that formed by stacking functional membranes 61A for adsorbing the interfering gas in a state intervened between 2 outer membranes 62, 62 composed of, for example, Teflon (registered trademark) as illustrated in FIG. 12 is used as the filter laminate 60A related to the gas sensor SD for detecting hydrocarbon gases in the measurement range of % LEL. In this embodiment, the functional membrane 61A has the 2-layer structure. However, no particular limitation is imposed on the number of membranes laminated.

Figure 13:
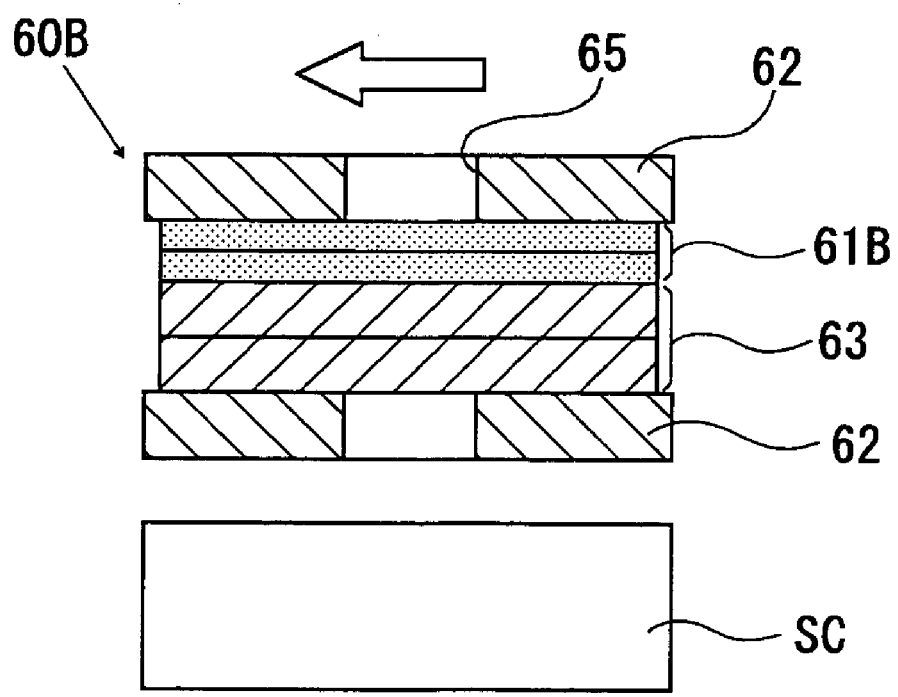
FIG. 13 is a cross-sectional view illustrating the construction of an exemplary filter laminate related to a gas sensor for detection of carbon monoxide gas.

The filter laminate 60B related to the gas sensor SC for detecting carbon monoxide gas is formed by stacking functional membranes 61B for adsorbing, for example, hydrogen sulfide gas, which is an interfering gas component, and active carbon layers 63 located on a lower side of the functional membranes 61B in a direction introducing a gas to be detected in a state intervened between 2 outer membranes 62, 62 as illustrated in FIG. 13. In this embodiment, 2 layers of the each functional membrane 61B and active carbon layer 63 are stacked. However, no particular limitation is imposed on the number of membranes and layers laminated. An arrow in FIGS. 12 and 13 indicates a flowing direction of a gas to be detected.

A viewing hole 65 for checking the degree of stain of the functional membrane 61A or 61B visually is formed in a part, for example, a central portion, of each of the outer membranes 62, 62 making up the filter laminate 60A or 60B, whereby the degree of stain of the functional membrane 61A or 61B can be checked visually from the outside even in a state that the filter assembly 50 is fitted to the sensor cap 30, since the filter cap 53 has transparency, so that the time the filter laminate 60 is exchanged can be easily known.

As described above, the rear half portion in the interior of the housing 10 is provided as a battery part region.

In the battery part region, a battery chamber 70 opened to the back surface of the housing 10, in which either one of 3 AA-sized (ANSI standard) dry cells 74, 74, 74 or a chargeable battery pack 90, which will be described subsequently, is installed exchangeably with the other, is formed.

On the back surface of the housing 10, a cover lid 80 for the battery chamber is provided at an opening portion of the battery chamber 70 closeably by a lid locking member 81 provided at a rear end of the housing 10.

Figure 14:
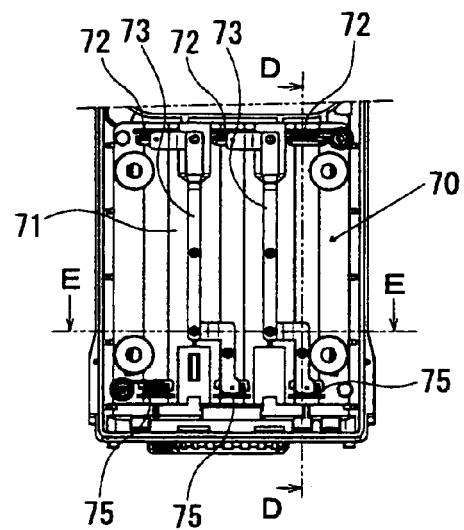
FIG. 14 is a plan view illustrating the construction of a battery chamber.
Figure 15:
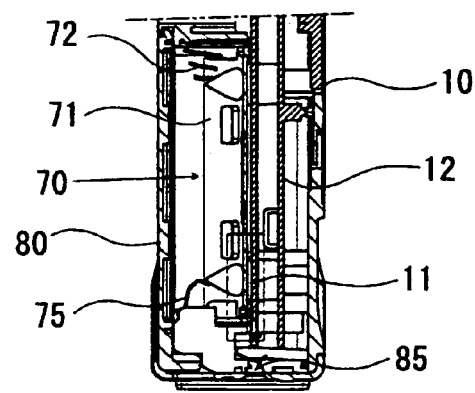
FIG. 15 is a cross-sectional view taken along line D—D in FIG. 14.
Figure 16:
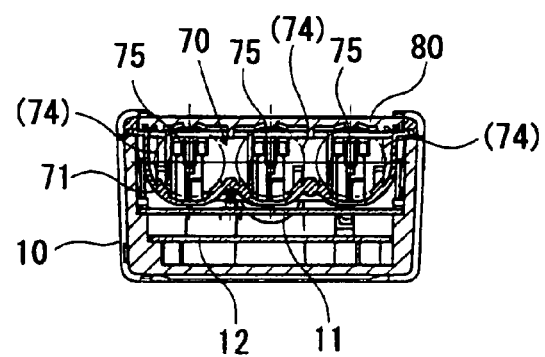
FIG. 16 is a cross-sectional view taken along line E—E in FIG. 14.

As illustrated in FIGS. 14 to 16, a receiving and supporting part 71, which comes into contact with a part of a peripheral surface of each of the dry cells 74, 74, 74 to support it, is formed in the battery chamber 70. On a fore-end end surface of the battery chamber 70, are arranged 3 negative-side terminal armatures 72, 72, 72 corresponding to the respective dry cells 74, 74, 74, and 3 positive-side terminal armatures 75, 75, 75 are arranged on a rear end surface thereof oppositely to the negative-side terminal armatures 72, 72, 72. The respective dry cells 74, 74, 74 are installed in the receiving and supporting part 71 in a state that the positive electrodes and negative electrodes thereof are turned to the same directions as one another, so as to be connected in series by connecting armatures 73, 73 arranged so as to extend along the longitudinal direction of the dry cell. By this constitution, the dry cells 74 are surely prevented from being installed in wrong direction.

Figure 17:
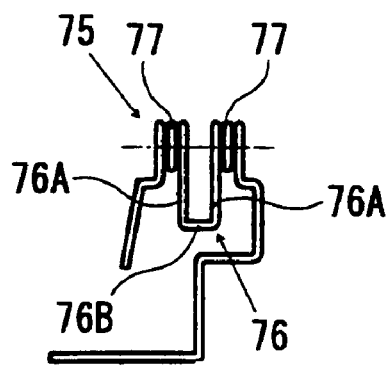
FIG. 17 is a front elevation illustrating the construction of a positive-side terminal armature.
Figure 18:
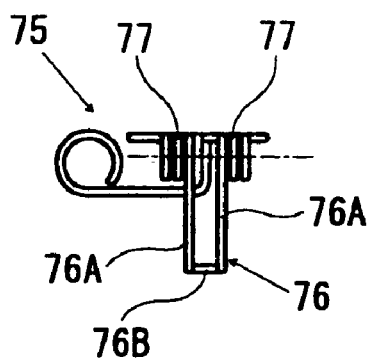
FIG. 18 is a top view of the positive-side terminal armature shown in FIG. 17.
Figure 19:
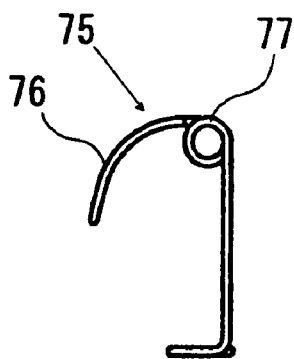
FIG. 19 is a side elevation of the positive-side terminal armature shown in FIG. 17.
Figure 20:
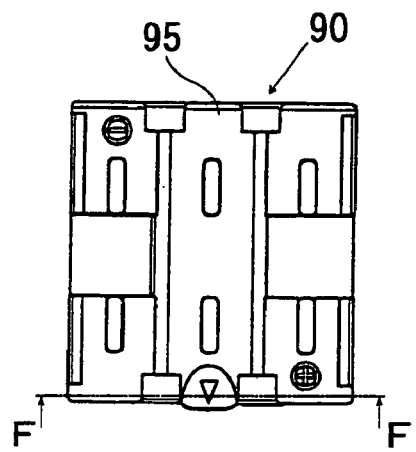
FIG. 20 is a plan view illustrating the construction of an exemplary chargeable battery pack.
Figure 21:
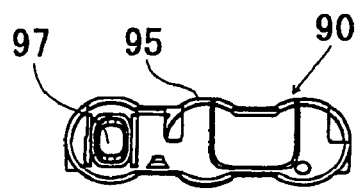
FIG. 21 is a top view of the chargeable battery pack shown in FIG. 20.
Figure 22:
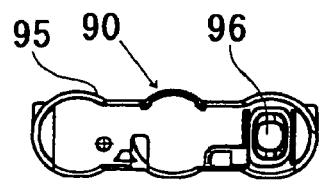
FIG. 22 is a bottom view of the chargeable battery pack shown in FIG. 20.
Figure 23:
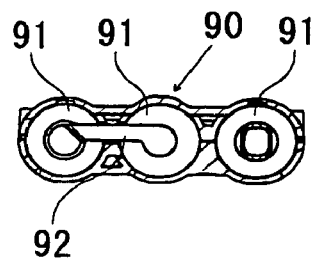
FIG. 23 is a cross-sectional view taken along line F—F in FIG. 20.

As illustrated in FIGS. 17 to 19, the positive-side terminal armature 75 is formed by deforming a metallic wire rod having elasticity and has a reversed U-shaped central contact arm portion 76, which forms a contact with the dry cell 74 or the chargeable battery pack 90, and 2 coil portions 77, 77 respectively connected to both ends of the central contact arm portion 76.

The coil portions 77, 77 each have the same center axis extending in a direction normal to the longitudinal direction of the dry cell 74.

The central contact arm portion 76 is of a reversed U shape composed of 2 parallel portions 76A, 76A and a linking arc portion 76B for linking both tips of the parallel portions 76A, 76A to each other. The 2 parallel portions 76A, 76A are greatly projected outward in a radial direction of the coil portions 77, 77 and curved in the form of an arc in a plane normal to the center axis of the 2 coil portions 77, 77. Specifically, the 2 parallel portions 76A, 76A are curved on an axis extending in parallel with the center axis of the coil portions 77, 77 and along a peripheral surface of a column having a diameter greater than the coil portions 77, 77.

No particular limitation is imposed on the negative-side terminal armature 72, and it is formed by, for example, a spiral type spring armature heretofore used.

The displacement by the positive-side terminal armature 75 in the longitudinal direction of the dry cell 74 is set in such a manner that the size of excess dimensions of the chargeable battery pack 90 to the dry cells 74 can be absorbed by displacement without greatly increasing the size of the terminal armature itself compared with the spiral type spring armature. When the total degree of displacement by the positive-side terminal armature 75 and the negative-side terminal armature 72 is, for example, at least 5 mm, the chargeable battery pack 90 can be surely installed in a state that sufficient electrical connection has been achieved.

As illustrated in FIGS. 20 to 23, the chargeable battery pack 90 is formed by integrally holding 3 rod-like chargeable batteries (storage batteries) 91, 91, 91 having the same external form as the AA-sized (ANSI standard) dry cell 74 by a holding frame member 95 in a state that the positive electrodes and negative electrodes of batteries adjacent to each other have been turned to reverse directions to each other so as to be connected in series by connecting armatures 92.

The holding frame member 95 has a sectional form adapted to the form of a space in a section crossing at a right angle to the longitudinal direction of the battery chamber 70. A positive terminal 96 is formed at a rear end surface (lower end surface in FIG. 20) thereof, and a negative terminal 97 is formed at a fore-end surface (upper end surface in FIG. 20) thereof.

In the gas detector described above, terminals 85 for charging for the chargeable battery pack are formed on, for example, a rear end surface of the housing 10 in an exposed state, whereby a charging operation can be conducted in a state that the chargeable battery pack 90 has been installed in the battery chamber 70. Accordingly, there is no need to conduct a complicated process, for example, a process, in which the chargeable battery pack 90 installed in the gas detector is taken out once, the battery pack is subjected to a charging operation using proper battery charger, and this pack is then installed again in the battery chamber 70, so that high convenience for use can be achieved.

The circuit board 11 for control preferably has a function of judging which of the dry cells 74 and the chargeable battery pack 90 is installed in the battery chamber 70 by detecting the number of terminals that electrical connection has been achieved. Specifically described, when the dry cells 74 are installed in the battery chamber 70, all the 6 terminal armatures are in a state that electrical connection has been achieved. When the chargeable battery pack 90 is installed in the battery chamber 70 on the other hand, 2 terminal armatures are in a state that electrical connection has been achieved. Which of the dry cells 74 and the chargeable battery pack 90 is installed in the battery chamber 70 can be judged by detecting these states.

When the dry cells 74 are installed in the battery chamber 70, the dry cells 74 are thereby prevented from being charged even when the gas detector is fitted to a proper battery charger by mistake in a state that the dry cells 74 have been installed. Accordingly, the gas detector can be provided with high safety.

In the gas detector described above, a gas to be detected ejected from the gas suction pump 41 is passed through the gas flowing path 35 formed in the interior of the sensor cap 30 and successively fed to the gas sensors SA to SE to conduct detection of the object gases to be detected and the kinds and concentrations of gases detected is displayed on the display part 13. When the fact that the concentration of any object gas to be detected has exceeded a reference value is detected, an alarm is raised by light emission of the light emitting parts 14 for alarm.

For example, the reference value in the case where an object gas to be detected is oxygen gas ($O_2$ gas) is preset to, for example, 18.0% by volume (vol %). When the concentration becomes lower than this reference value, an alarm actuating signal is outputted. The reference value in the case where an object gas to be detected is a hydrocarbon gas (HC gas) is preset to, for example, 10% LEL (gas concentration to a level of explosion limit). The reference value in the case where an object gas to be detected is carbon monoxide gas (CO gas) is preset to, for example, 25 ppm, and the reference value in the case where an object gas to be detected is hydrogen sulfide gas ($H_2S$ gas) is preset to, for example, 10 ppm. When the concentration exceeds any of these reference values, an alarm actuating signal is outputted.

Alarm annunciating mechanisms may take a structure that an alarm buzzer and a vibration generator (emitting low cycles of about several tens Hz) for alarm are provided. In this case, an alarm is raised by buzzer sound by the alarm buzzer, light emission by the light emitting element for alarm and vibration by the vibration generator for alarm, respectively.

When plural kinds of alarm annunciating mechanisms are provided, it is not necessary to drive all the alarm annunciating mechanisms at the same time, and it is preferable to conduct a cyclic alarm operation that the respective alarm annunciating mechanisms are successively driven only for a predetermined period of time. According to such drive control, the consumption of the dry cells or batteries can be inhibited compared with the case where the alarm annunciating mechanisms are driven at the same time.

According to the gas detector described above, the housing 10 has the form holdable by grasping with a hand, and all the necessary component members are rationally arranged in a state that a dead space within the housing 10 is reduced as much as possible, so that the gas detector itself can be fabricated into a small-sized one while surely retaining necessary functions.

In other words, the 5 gas sensors SA to SE are held in a state received to the sensor holder 20 having the gas sensor-arranging region of the L shape as a whole, the gas sucking pump 41 is installed in the fore-end of the pump unit-installing part 21 in the sensor holder 20, and the pump driving motor 42 is arranged along the side surface of the pump unit-installing part 21, thereby, substantially preventing the gas sucking pump 41 and pump driving motor 42 from projecting from the peripheral edge of the circuit board 11 for control. The pump unit 40 is contained in the region, the 2 directions of which is sectioned by the gas sensor-arranging region, whereby the 5 gas sensors SA to SE and the pump unit 40 are compactly arranged, so that the space occupied by these members in the housing 10 can be lessened as much as possible, and so the gas detector itself can be fabricated as a small-sized one. Accordingly, excellent portability and high convenience for use can be achieved.

In addition, the gas detector has the so-called common battery chamber 70 formed in such a manner that either one of the dry cells 74 or the chargeable battery pack 90 can be installed exchangeably with the other, whereby both dry cells (primary cells) and chargeable batteries (secondary batteries) can be used without using any attachment such as an adaptor.

Further, since comparatively great power is ensured as a power source for driving, at least one of the gas sensors can be provided as one of the contact combustion type, so that the degree of freedom of selection of detectable gas components becomes high, and high convenience for use can be achieved.

Although the preferred embodiments of the present invention have been described above, the present invention is not limited to the embodiments described above, and various changes and modifications may be added thereto.

For example, it is only necessary to form the functional part region in the foreside half portion within the housing of the gas detector and the battery part region in the rear half portion, and other members can be freely arranged. Dry cells used as a power source are not limited to the AA-sized (ANSI standard) dry cells.

The gas detector may be used by holding it with a hand, or by being fitted directly to a person's body or to a person's wear using a proper fitting member. As examples of the fitting member, may be mentioned a clip and a pin. The fitting member may be formed integrally with the housing according to the form thereof. The fitting member may be formed in an easily exchangeable shape.

The filter assemblies may be classified by coloring according to the functions thereof, i.e., the kinds of interfering gas components that can be removed, whereby proper filter assemblies corresponding to the gas sensors can be surely installed, and so gas detection can be conducted with high reliability.

The gas detector may also be so constructed that a communication terminal for reading out concentration data of gases detected by the gas detector is provided. In, for example, FIG. 3, an aperture plate for infrared communication is indicated by reference numeral 19. According to such construction, the concentration data of the gases can be read out while conducting, for example, a charging operation of the gas detector.

What is claimed is:

1. A portable gas detector comprising:
   a housing shaped as a slim and substantially flat box that is adapted to be grasped by a user's hand, said housing including a functional part region, in which functional members related to a gas detecting operation are arranged, at a fore-side of the housing, and a battery part region, in which a power source for driving the functional members is arranged, at a rear portion of the housing;
   a plurality of gas sensors arranged in an L-shape, in the functional part region, such that one of the sensor is provided at a corner of the L-shape and such that a plurality of gas sensors are provided in each of two extending portions of the L-shape that. extend from the corner;
   a gas suction mechanism which sucks gas from outside of the gas detector into the housing to be exposed to the gas sensors, and which is provided in a space at an interior of the L-shape such that the space is bordered on two sides by the two extending portions of the L-shape; and
   a sensor cap which covers the sensort and which comprises a gas flowing path extending therethrough, a plurality of gas inlet passages corresponding respectively to the gas sensors to expose the gas sensors to the gas traveling through the gas flowing path, and an input section through which the gas sucked into the housing is input to the gas flowing path.

2. The portable gas detector according to claim 1, further comprising a sensor holder comprising sensor holding parts for holding the gas sensors in a plane in the L-shape.

3. The portable gas detector according to claim 1 or 2, wherein at least one of the plurality of the gas sensors comprises a contact combustion type gas sensor element, and wherein a voltage of 4.5 V is supplied from the power source.

4. The portable gas detector according to claim 1, wherein a battery chamber is formed in the battery part region in an interior of the housing so as to be openable to be exposed at a back surface of the housing, and wherein the battery chamber interchangeably holds one of: (i) 3 rod-like dry cells, and (ii) a chargeable battery pack formed by 3 chargeable batteries held in parallel by a holding frame member to have substantially a same external shape as dry the cell batteries.

5. The portable gas detector according to claim 1 or 2, wherein the gas suction mechanism comprises an exhaust flow path, and a pressure sensor is connected to the exhaust flow path and is positioned in said space at the interior of the L-shape.

6. The portable gas detector according to claim 3, wherein the gas suction mechanism comprises an exhaust flow path, and a pressure sensor is connected to the exhaust flow path and is positioned in said space at the interior of the L-shape.

7. The portable gas detector according to claim 4, wherein the gas suction mechanism comprises an exhaust flow path, and a pressure sensor is connected to the exhaust flow path and is positioned in said space at the interior of the L-shape.

8. The portable gas detector according to claim 1, wherein the sensor cap comprises an internal-Side cap member and an external-side cap member stacked on the internal-side cap member;
wherein the gas inlet passages are formed in the internal-side cap member, which is positioned nearer to the gas sensors than the external-side cap member; and
wherein the gas flowing path is provided in a portion of a face where the internal-side cap member meets the external-side cap member.

9. The portable gas detector according to claim 1, wherein the sensor cap comprises at least one filter-installing part therein, in which a filter assembly is installed at a position corresponding to one of the gas sensors, and wherein the filter assembly adsorbs at least one interfering gas component other an object gas component to be detected by the gas sensor corresponding thereto.

10. The portable gas detector according to claim 4, wherein the battery chamber comprises a plurality of negative-side terminal armatures and a plurality of positive-side terminal armatures, and wherein each of the positive-side terminal armatures comprises:
- a central contact arm portion which is substantially U-shaped, said U-shape including two parallel portions and a linking portion linking the parallel portions, and said two parallel portions being curved; and
- two coiled portions having a same center axis which are respectively connected to the parallel portions of the central contact arm portion.

* * * * *